United States Patent [19]
Lamont

[11] Patent Number: 5,226,245
[45] Date of Patent: Jul. 13, 1993

[54] PROTECTIVE BOOT STRUCTURE

[76] Inventor: William D. Lamont, 54283 Meadowood Ct., Shelby Township, Maccomb County, Mich. 48316

[21] Appl. No.: 763,335

[22] Filed: Sep. 20, 1991

[51] Int. Cl.$^5$ .................... A43B 1/02; A43B 1/10; A43B 7/14
[52] U.S. Cl. .......................... 36/9 R; 36/93; 128/892
[58] Field of Search ............... 36/88, 89, 91, 93, 9 R, 36/71, 110; 128/882, 892, 894

[56] References Cited

U.S. PATENT DOCUMENTS

| | | | |
|---|---|---|---|
| Re. 33,090 | 10/1989 | Berguer | 36/9 R |
| 2,911,657 | 10/1959 | Streeter, III | 5/327 |
| 3,237,319 | 3/1966 | Hanson | 36/89 |
| 3,462,763 | 8/1969 | Schneider et al. | 2/DIG. 6 |
| 3,511,233 | 5/1970 | Holy, Jr. | 128/149 |
| 3,529,369 | 9/1970 | Drago | 36/120 |
| 3,552,044 | 1/1971 | Wiele | 36/71 |
| 3,606,884 | 9/1971 | Peter | 128/80 |
| 3,693,270 | 9/1972 | Murray | 36/71 |
| 3,750,310 | 8/1973 | Messner et al. | 36/93 |
| 4,076,022 | 2/1978 | Walker | 128/149 |
| 4,197,845 | 4/1980 | Berguer | 128/149 |
| 4,472,890 | 9/1984 | Gilbert | 36/29 |
| 4,478,214 | 10/1984 | Lamont | 128/149 |
| 4,813,162 | 3/1989 | Harris | 36/11.5 |
| 4,841,648 | 6/1989 | Shaffer et al. | 36/91 |
| 5,092,347 | 3/1992 | Shaffer et al. | 128/892 |

FOREIGN PATENT DOCUMENTS 496056  11/1938  United Kingdom ................ 36/71

Primary Examiner—Steven N. Meyers
Attorney, Agent, or Firm—Charles W. Chandler

[57] ABSTRACT

A protective boot for patients with arterial disease. The boot includes a separate fluid-containing cushion which can be attached in a variety of positions on or in the boot to provide support for the patient's foot and leg when bed-ridden.

13 Claims, 2 Drawing Sheets

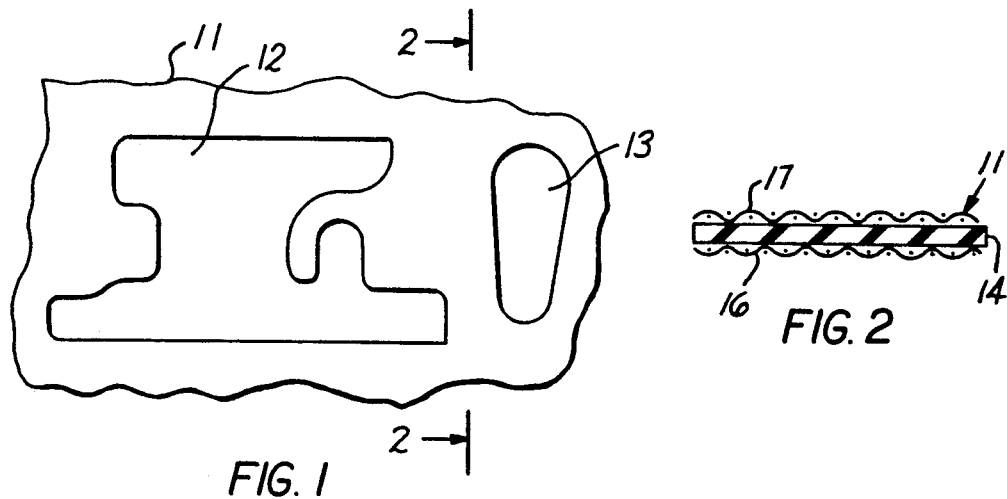
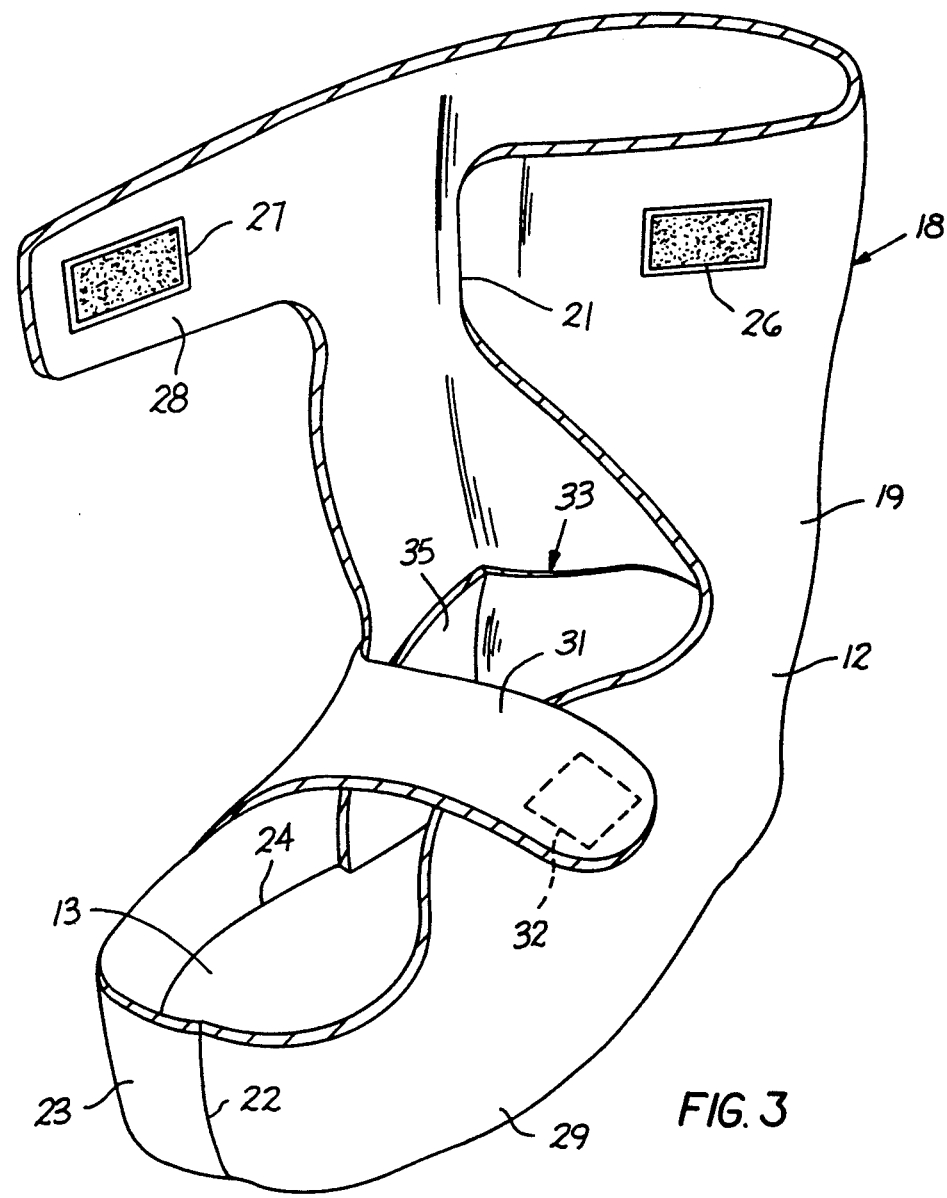

PROTECTIVE BOOT STRUCTURE

BACKGROUND OF THE INVENTION

1. Field of the Invention:

This invention relates to a protective boot for the comfort and protection of a patient who, if not entirely bedfast, must spend so much time there as to be in danger of incurring decubitus ulcers or other forms of trauma. In particular, the invention relates to a boot capable of use both in bed and during a limited amount of ambulation and having a fluid-containing cushion with releasable attachment means to allow it to be positioned on or within the boot wherever needed to provide support for the patient's foot and leg. The cushion has an enclosed fluid-filled core to allow the cushion to conform comfortably to any part of the patient's foot or lower leg that may be pressed against it while the patient is lying down.

2. Description of Relevant Art:

My prior U.S. Pat. No. 4,478,214 describes a soft boot that is designed to protect a patient's foot from trauma, abrasions, decubitus ulcer formation, moisture accumulation, external pressures, heat loss, etc. during both bedridden and ambulatory conditions. The boot is generally open at the front, except for an integral closure portion, and has a rigid liner that extends along the sole to a point beyond the user's toes and is bent up at the front. The boot has a fluid cushion built into a fixed location in the lower rear part of the boot to engage the patient's heel cord and support the back portion of the patient's leg. Sides of the cushion also extend a short distance along the side of that portion to give added protection and comfort.

An ulcer-prevention device shown by Browning in U.S. Pat. No. 4,197,845 is made of cloth and is shaped generally like a sock, the toe and heel of which have been removed and which is openable along the front to receive a patient's foot. The front edges have Velcro fasteners to hold them together after the device has been placed on the patient's foot. A fluid-filled cushion is held by straps normally attached to the back of the device behind the user's ankle to support the heel out of contact with the bed. The fluid-filled cushion can, alternatively, be attached to any place on the device to elevate selected parts of the patient's foot so as to prevent those parts from pressing against the bed.

U.S. Pat. No. Re. 33,090 to Berguer describes a boot formed of a double layer of laminated material with a foam insert built into a fixed location between the layers at the lower back part of the boot and extending forward slightly along the sides of the boot to support the patient's heel cord. Each layer of the laminated material comprises a sheet of foam material and a flexible cover sheet. In the finished boot, the two foam layers face each other and are enclosed between their respective cover sheets, one of which thus constitutes the outermost part of the boot, while the other constitutes the innermost part. Seams at the toe and around the periphery of the sole are sewn facing outwardly, which makes it possible that they may come in contact with the patient's other foot.

Other devices to support patient' feet and ankles are described by Streeter in U.S. Pat. No. 2,911,657; Holy, Jr. in U.S. Pat. No. 3,511,233; Peter in U.S. Pat. No. 3,606,884; and Walker in U.S. Pat. No. 4,076,022.

OBJECTS AND SUMMARY OF THE INVENTION

It is an object of this invention to provide an improved medical boot for adjustable, comfortable support and protection for a patient required to spend a substantial part of their time in bed.

Another object is to provide convenient means for easily changing the location and extent of support of the foot and lower leg portion of a patient to prevent the formation of decubitus ulcers and other kinds of discomfort and trauma.

A further object is to provide a medical boot with a removable, padded reinforcing plate that can be easily removed to make ambulation easier for the patient.

A medical boot made in accordance with this invention comprises a substantially boot-shaped main body and a pillow that contains a fluid-containing cushion and is releasably attachable to selected locations on both the internal and external surface of the main body to increase the patient's comfort and to minimize the possibility of forming decubitus ulcers. The main body includes a foot portion and an upper portion that extends above the user's ankle. Both portions, as well as the pillow, are formed primarily of substantially soft, flexible, compressible, shape-retaining material bonded surface-to-surface to a layer of soft, smooth, non-allergenic cloth, such as moleskin. The pillow has a central recess, in which the fluid-containing cushion is enclosed, and panels on each side of the central part. The panels can either be spread out to cushion sides of the patient's ankle, or one or both panels can be folded over the central part to increase its thickness.

The fluid-containing cushion is typically a soft plastic envelope that can be filled with water or air, and its thickness and firmness as a cushion can be increased by folding one part of the envelope over another part.

The invention will be described in greater detail in connection with the drawings, in which like serial numbers in different figures indicate the same item.

BRIEF DESCRIPTION OF THE DRAWINGS

FIG. 1 shows a panel of material on which components of the boot of this invention are indicated.

FIG. 2 is a cross-sectional view of a fragment of the panel in FIG. 1.

FIG. 3 is a perspective view of the boot of this invention.

DETAILED DESCRIPTION OF A PREFERRED EMBODIMENT

Figure 4:
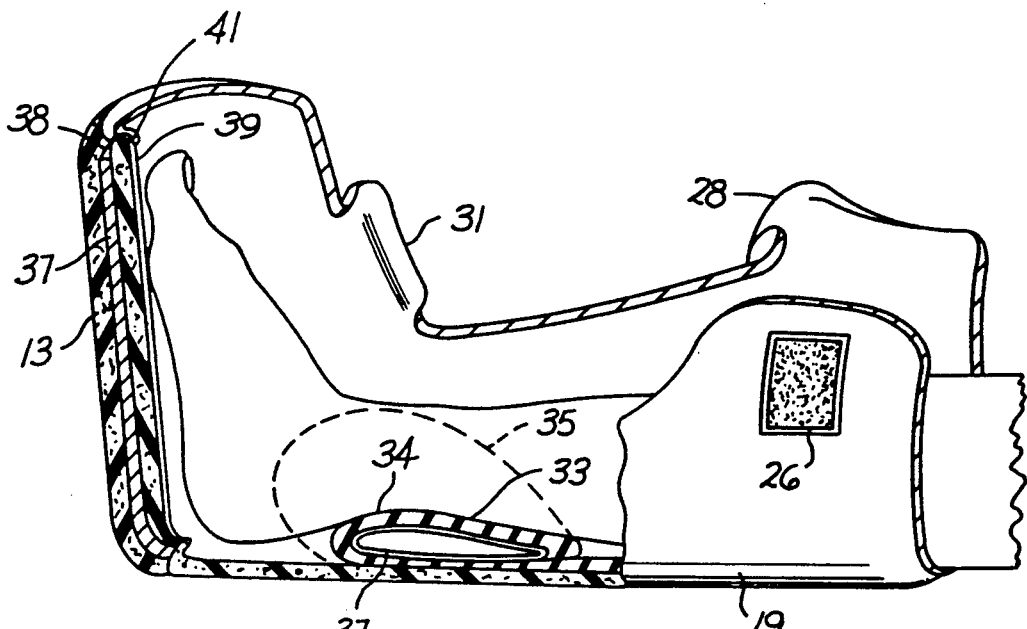
FIG. 4 is a side view of the boot in FIG. 3 with parts broken away to show the internal structure.

FIGS. 1 and 2 show a multi-layer sheet 11 on which outlines of panels 12 and 13 to be used in making boot components are laid out. The sheet 11 consists of a layer 14 of elastomeric, shape-retaining material, such as soft, flexible, compressible open-cored polyurethane foam, or the like, with layers 16 and 17 of ultra-smooth, soft, non-allergenic cloth, such as moleskin, adhesively bonded to the surfaces of the layer 14. For the sake of simplicity of description, the layers 16 and 17 will be referred to hereinafter as moleskin, although it is to be understood that another type of soft cloth or clothlike material may be used instead.

FIG. 3 shows a boot 18, the upper part 19 of which is formed of the panel 12 and the sole of which is formed by the panel 13. One of the layers 16 or 17 of moleskin will form the inner surface of the boot and the other the outer surface, thereby not only eliminating skin irritation of the foot on which the boot is placed but irritation of any other part of the patient's skin with which the outer surface of the boot may come in contact.

An overedge binding 21 is stitched around the entire common perimeter of the panel to strengthen the perimeter against fraying, as well as to provide a sturdy structure at a seam 22 at the front of the toe 23. A similar overedge binding 24 is formed around the perimeter of the panel 13 where it joins the bottom edge of the upper part. The boot is initially sewn together inside out and is then turned right side out to place the bindings, which can be rather abrasive, on the inside where they cannot rub against the patient's other leg.

The boot has a patch 26 of one form of hook-and-loop material located in the proper position on the upper part 19 to engage a patch 27 of the other form of hood-and-loop material on the surface of a leg strap 28, which is shown in the open position to receive a patient's leg. The patches 26 and 27 may be attached to their respective parts of the boot 18 by any suitable means. In this embodiment, the patch 26 is attached adhesively and the patch 27 is attached by being stitched to the leg strap.

The foot portion 29 of boot has another patch of one form of hook-and-loop material located in the proper position to engage a patch of the other type of hook-and-loop material near the end of the juxtaposed surface of a foot strap 31. This strap is shown in closed position, so that the patch on it is not visible, being on the under side and juxtaposed with the patch on the foot portion. However, the location of the patch on the foot strap is shown by a line of stitching 32 by which that patch is attached to the foot strap, and the cooperating patch is attached to the foot portion 29 directly below the foot strap patch.

This invention provides a pillow 33 with a central portion 34 and side panels 35 and 36, of which only the panel 35 is shown in FIG. 3. The central portion of the pillow is centered in the lower, rear, interior surface of the boot 18 in FIG. 3, but it is one of the features of this invention that the pillow 33 is releasably attached to the boot and can be moved to any location that makes the patient more comfortable or provides needed support, either on the inner surface, as shown in FIG. 3 or on the outer surface.

FIG. 4 shows the boot 18 on the foot of a patient in supine position with both the leg and foot straps 28 and 31, respectively, open. The pillow 33 is shown under the heel cord of the patient, as is appropriate to elevate the patient's heel away from the surface of the boot in order to avoid decubitus ulcer formation on the heel. The central part 34 of the pillow is in cross section, and it may be seen that it has an outer covering that consists of two layers of elastomeric, shape-retaining material, such as soft, flexible, compressible open-cored polyurethane foam, or the like between which there is a fluid-containing cushion of relatively soft, easily deformable material, such as polyurethane or the like. The pillow 33 is thus free to conform to the contours of the portion of the patient's leg with which it comes in contact, thereby providing maximum comfort, yet the fluid-containing pillow does not take a set configuration after prolonged pressure, as does the elastomeric material frequently used heretofore in medical boots.

FIG. 4 shows the arrangement of the foot portion 29 of the boot 18. This an open-toed design, which allows the patient's foot to be ventilated more easily, and thereby not only keeps the patient more comfortable but also reduces moisture accumulation. In addition, the open-toed design permits easy visual inspection and pulse checks of the patient's foot by medical personnel.

The sole of the boot is shown to have several layers. The outer layer is the panel 13, and its binding 24 is shown to be turned inwardly, as previously described. In addition, a sturdy inner sole is provided to help prevent foot-drop by maintaining normal foot positioning. In this embodiment, the inner sole includes a plate 37 of relatively rigid material, such as cardboard about $\frac{1}{8}$" thick and a pad 38 of foam material, one surface of which is bonded adhesively to the plate and the other surface of which has a layer 39 of moleskin or the like bonded to it. As in the other parts formed of a sheet of moleskin or the like bonded to a sheet of foam material, the periphery of the pad is defined by overedge stitching 41. The inner sole consisting of the plate 37 and the pad 38 is not attached to the rest of the foot portion 29 except by being fitted in snuggly, and it can be easily removed for better ambulation. When the patient is supine, the plate 37, which extends beyond the ends of the patient's toes, protects the patient's foot against pressure from bedclothing. The construction of the boot, with its firm, anti-slip sole, permits secure, comfortable ambulation for the patient.

Figure 5:
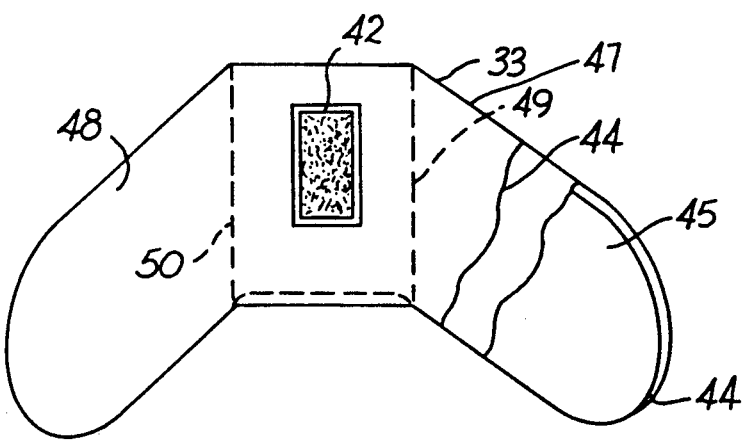
FIG. 5 shows a detachable support component for the boot in FIG. 3 with parts broken away to reveal the inner structure.

The fluid-containing pillow 33 is shown in greater detail in FIG. 5, which is a rear view to show a patch of hook material 42. Such material normally engages loop material, but the minute hooks can also lock onto the soft moleskin in which the entire boot 18 is covered. This makes it possible to place the pillow in any location on either the inner surface or the outer surface of the boot, as required to obtain the greatest comfort or provide the necessary support for the patient. In most cases, it is likely that the pillow would be in the position shown in FIG. 4, but if the patient were forced to lie face down, the pillow 33 could be placed on the front portion, for example in the area of the leg strap. It could also be placed on the sides of the boot.

The pillow 33 comprises front and rear coverings, each of which consists of a layer 43 of moleskin 44 covering and adhesively joined to a layer 44 substantially soft, flexible, compressible shape-retaining material 45 defining a main pillow portion 46 and side panels 47 and 48 extending symmetrically from the main pillow portion. The main portion 46 has a lateral dimension bounded by two seams 49 and 50, and the side panels preferably extend outwardly from the main portion 46 in the opposite lateral directions by at least substantially the same distance as the lateral dimension of the main portion. This permits either or both panels 47 and 48 to be folded across the main portio 46 to increase the thickness of the pillow, if necessary.

Figure 6:
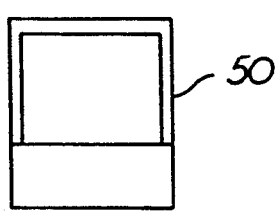
FIG. 6 is a front view of a fluid-filled container for use in the support in FIG. 5.
Figure 7:
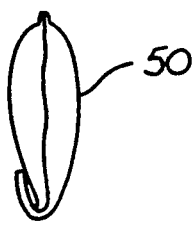
FIG. 7 is a side view of the container in FIG. 6.

The main portion defines a central recess in which is placed an easily deformable, fluid-containing, container 50 shown in FIGS. 6 and 7. This container provides cushion means for obtaining soothing water flotation of the patient's heel and leg, and it also provides ankle bone protection. In addition, it does not take a set as the foam material currently used in some ankle supports is likely to do. The container is made of relatively soft plastic material, such as polyethylene and has a certain normal maximum volume. However, in accordance with this invention, it is not normally filled to its full capacity. This leaves it sufficiently compliant to fit the contours of the patient's foot or ankle or an bandages or other devices thereon. If it is desired to make it thicker, at the expense of making it harder, one end 51 may be folded over before it is placed in the central recess in the pillow 33.

The invention has been described in terms of a specific embodiment, but it will be apparent to those skilled in the art that modifications may be made therein without departing from the true scope of the invention.

What is claimed is:

1. A medical boot, comprising:
   a substantially boot-shaped main body portion formed primarily of substantially soft, flexible, compressible, shape-retaining material;
   pillow means for cushioning and supporting the limb of a user, comprising:
     an outer covering of substantially soft, flexible, compressible, shape-retaining material defining a main pillow portion with a recess, and a pair of side panels extending from the main pillow portion, each side panel being foldable with respect to the main pillow portion;
     an easily deformable, fluid-containing cushion disposed within the recess; and
     attachment means for releasably connecting the pillow means to a selected location on the boot-shaped main body portion.

2. A medical boot as defined in claim 1, in which the boot-shaped main body portion has a heel and a top opening, and the pillow means has a length substantially less than the distance between the heel and the top opening, whereby the main pillow portion may be located in a selected location between the heel and the top opening of the boot on the inner side thereof to accommodate the configuration of the heel of a user and to support the back of a bedridden user's leg.

3. A medical boot as defined in claim 1, including a sole of a relatively stiff material mounted in the inside bottom of the boot-shaped main body portion and removable from the main body portion to permit the user to ambulate with the boot.

4. A medical boot as defined in claim 1, in which the side main pillow portion has a generally rectangular configuration, and the pair of side panels are connected along opposite side edges of the main pillow portion by a linear fold line, and each of the side panels has a configuration defined by the fold line, a second linear side edge forming an acute angle with and having one end intersecting the fold line, and a generally curved border continuing from the opposite end of the second linear side edge.

5. The medical boot of claim 1 in which the releasable attachment means comprises hook-and-loop means attached to the pillow means.

6. The medical boot of claim 2 comprising a plurality of said pillow means.

7. The medical boot of claim 1 in which the outer covering of the pillow means comprises a composite layer of soft, flexible, compressible, shape-retaining foam material bonded to a layer of ultra-smooth, soft, non-allergenic cloth.

8. The medical boot of claim 7 in which the cloth is moleskin.

9. The medical boot of claim 1 in which the recess in the pillow means is centrally located and is defined by longitudinal seams on each side of the main pillow portion and has a predetermined longitudinal dimension, and the side panels extend laterally outward beyond the seams and comprise lobes extending longitudinally beyond the recess.

10. The medical boot of claim 6 in which the side panel means comprise one side panel on each side of the recess, and the lobes are at one longitudinal end of each side panel.

11. The medical boot of claim 7 in which the side panels are substantially symmetrical about the main pillow portion.

12. A medical boot, comprising:
    a substantially boot-shaped main body portion formed primarily of substantially soft, flexible, compressible, shape-retaining material;
    pillow means for cushioning and supporting the limb of a user, comprising:
      an outer covering of substantially soft, flexible, compressible, shape-retaining material defining a main pillow portion with a recess, and a pair of side panels extending from the main pillow portion;
      an easily deformable, fluid-containing cushion within the recess;
      the main pillow portion having a substantially rectangular configuration including a pair of substantially parallel side edges forming a foldable seam line between each of the side panels and the main pillow portion;
      whereby each of the side panels may be folded over in a face-to-face relationship with the main pillow portion to increase the overall height of the pillow means; and
      attachment means for releasably connecting the pillow means in a selected location on the main body portion.

13. A medical boot, comprising:
    a substantially boot-shaped main body portion formed primarily of substantially soft, flexible, compressible, shape-retaining material and having an inside covering and an outside covering of moleskin;
    pillow means for cushioning and supporting the limb of a user, comprising:
      an outer covering of substantially soft, flexible, compressible, shape-retaining material defining a main pillow portion with a recess;
      an easily deformable, fluid-containing cushion disposed within the recess; and
      fabric hook means attached to the pillow means and engageable with the moleskin for releasably connecting the pillow means to a selected location on either the inside covering or the outside covering of the boot-shaped main body portion.

* * * * *